(12) United States Patent
Wendland et al.

(10) Patent No.: US 11,058,825 B2
(45) Date of Patent: Jul. 13, 2021

(54) CAP FOR AN INJECTION DEVICE

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 377 days.

(21) Appl. No.: 15/778,277

(22) PCT Filed: Nov. 21, 2016

(86) PCT No.: PCT/EP2016/078252
§ 371 (c)(1),
(2) Date: May 23, 2018

(87) PCT Pub. No.: WO2017/089263
PCT Pub. Date: Jun. 1, 2017

(65) Prior Publication Data
US 2018/0339112 A1 Nov. 29, 2018

(30) Foreign Application Priority Data
Nov. 27, 2015 (EP) ...................... 15196681

(51) Int. Cl.
*A61M 5/32* (2006.01)
(52) U.S. Cl.
CPC ........ *A61M 5/3202* (2013.01); *A61M 5/3204* (2013.01); *A61M 5/3245* (2013.01); *A61M 5/3257* (2013.01); *A61M 2005/3254* (2013.01)

(58) Field of Classification Search
CPC .............. A61M 5/3202; A61M 5/3204; A61M 5/3245; A61M 5/3257; A61M 2005/3254
See application file for complete search history.

(56) References Cited

U.S. PATENT DOCUMENTS 3,967,621 A 7/1976 Schwarz
5,116,319 A 5/1992 van den Haak
(Continued)

FOREIGN PATENT DOCUMENTS

FR 2278350 2/1976
WO WO 2012/003516 1/2012

OTHER PUBLICATIONS

PCT International Preliminary Report on Patentability in International Appln. No. PCT/EP2016/078252, dated May 29, 2018, 6 pages.
(Continued)

*Primary Examiner* — Theodore J Stigell
*Assistant Examiner* — Rachel T. Smith
(74) *Attorney, Agent, or Firm* — Fish & Richardson P.C.

(57) ABSTRACT

The present disclosure relates to a cap for an injection device. The injection device comprises a body for holding a syringe having a needle extending from an end thereof. The cap is removably attachable to the body. The cap comprises an actuator and a needle shield to cover said needle. The cap further comprises a coupling between the actuator and the needle shield. The coupling is configured such that when the cap is attached to the body of an injection device axial movement of the actuator away from the body causes rotation of the needle shield relative to the body.

17 Claims, 5 Drawing Sheets

(56) References Cited

U.S. PATENT DOCUMENTS

| | | | |
|---|---|---|---|
| 5,147,326 A | 9/1992 | Talonn et al. |
| 5,183,469 A | 2/1993 | Capaccio |
| 5,254,099 A | 10/1993 | Kuracina et al. |
| 5,320,609 A | 6/1994 | Haber et al. |
| 5,336,197 A | 8/1994 | Kuracina et al. |
| 5,447,500 A | 9/1995 | Bergstresser et al. |
| 5,480,385 A | 1/1996 | Thorne et al. |
| 5,487,734 A | 1/1996 | Thorne et al. |
| 5,514,097 A | 5/1996 | Knauer |
| 5,542,927 A | 8/1996 | Thorne et al. |
| 5,545,145 A | 8/1996 | Clinton et al. |
| 5,549,708 A | 8/1996 | Thorne et al. |
| 5,584,816 A | 12/1996 | Gyure et al. |
| 5,616,135 A | 4/1997 | Thorne et al. |
| 5,656,031 A | 8/1997 | Thorne et al. |
| 5,709,662 A | 1/1998 | Olive et al. |
| 5,820,621 A | 10/1998 | Yale et al. |
| 5,823,997 A | 10/1998 | Thorne |
| 5,829,589 A | 11/1998 | Nguyen et al. |
| 5,833,669 A | 11/1998 | Wyrick |
| 5,836,917 A | 11/1998 | Thorne et al. |
| 5,928,200 A | 7/1999 | Thorne et al. |
| 5,935,104 A | 8/1999 | Janek et al. |
| 5,941,857 A | 8/1999 | Nguyen et al. |
| 5,980,488 A | 11/1999 | Thorne |
| 6,024,727 A | 2/2000 | Thorne et al. |
| 6,210,369 B1 | 4/2001 | Wilmot et al. |
| 6,221,053 B1 | 4/2001 | Walters et al. |
| 6,258,068 B1 | 7/2001 | Kirchhofer et al. |
| 6,280,420 B1 | 8/2001 | Ferguson et al. |
| 6,280,421 B1 | 8/2001 | Kirchhofer et al. |
| 6,290,679 B1 | 9/2001 | Hostettler et al. |
| 6,454,746 B1 | 9/2002 | Bydlon et al. |
| 6,485,470 B2 | 11/2002 | Hostettler et al. |
| 6,575,939 B1 | 6/2003 | Brunel |
| 6,620,137 B2 | 9/2003 | Kirchhofer et al. |
| 6,726,661 B2 | 4/2004 | Munk et al. |
| 6,746,429 B2 | 6/2004 | Sadowski et al. |
| 6,796,968 B2 | 9/2004 | Ferguson et al. |
| 6,949,086 B2 | 9/2005 | Ferguson et al. |
| 6,979,316 B1 | 12/2005 | Rubin et al. |
| 6,986,760 B2 | 1/2006 | Giambattista et al. |
| 7,112,187 B2 | 9/2006 | Karlsson |
| 7,128,728 B2 | 10/2006 | Kirchhofer et al. |
| 7,198,618 B2 | 4/2007 | Ferguson et al. |
| 7,314,464 B2 | 1/2008 | Giambattista et al. |
| 7,357,791 B2 | 4/2008 | Kirchhofer et al. |
| 7,500,963 B2 | 3/2009 | Westbye et al. |
| 7,637,889 B2 | 12/2009 | Glynn |
| 7,648,482 B2 | 1/2010 | Edwards et al. |
| 7,658,724 B2 | 2/2010 | Rubin et al. |
| 7,666,164 B2 | 2/2010 | Giambattista et al. |
| 7,744,582 B2 | 6/2010 | Sadowski et al. |
| 7,758,550 B2 | 7/2010 | Bollenbach et al. |
| 7,771,397 B1 | 8/2010 | Olson |
| 7,776,015 B2 | 8/2010 | Sadowski et al. |
| 7,780,637 B2 | 8/2010 | Jerde et al. |
| 7,815,611 B2 | 10/2010 | Giambattista et al. |
| 7,828,778 B2 | 11/2010 | Liversidge |
| 7,871,397 B2 * | 1/2011 | Schraga ............ A61M 5/3213 604/110 |
| 7,931,625 B2 | 4/2011 | Kirchhofer et al. |
| 7,931,626 B2 | 4/2011 | Kirchhofer et al. |
| 7,947,017 B2 | 5/2011 | Edwards et al. |
| 7,988,675 B2 | 8/2011 | Gillespie et al. |
| 8,002,756 B2 | 8/2011 | Walters et al. |
| 8,038,654 B2 * | 10/2011 | Lim .................. A61M 5/3216 604/192 |
| 8,048,035 B2 | 11/2011 | Mesa et al. |
| 8,062,252 B2 | 11/2011 | Alheidt et al. |
| 8,062,255 B2 | 11/2011 | Brunnberg et al. |
| 8,128,605 B2 | 3/2012 | Masi et al. |
| 8,366,682 B2 | 2/2013 | Wyrick |
| 8,382,713 B2 | 2/2013 | Glynn |
| 8,663,188 B2 | 3/2014 | Genosar et al. |
| 8,672,902 B2 | 3/2014 | Ruan et al. |
| 8,679,061 B2 | 3/2014 | Julian et al. |
| 8,858,508 B2 | 10/2014 | Lavi et al. |
| 9,486,581 B2 | 11/2016 | Lovell et al. |
| 2001/0009990 A1 | 7/2001 | Hostettler et al. |
| 2001/0021827 A1 | 9/2001 | Ferguson et al. |
| 2001/0039401 A1 | 11/2001 | Ferguson et al. |
| 2001/0044847 A1 | 11/2001 | Kirchhofer et al. |
| 2001/0049496 A1 | 12/2001 | Kirchhofer et al. |
| 2002/0045866 A1 | 4/2002 | Sadowski et al. |
| 2002/0133122 A1 | 9/2002 | Giambattista et al. |
| 2003/0014018 A1 | 1/2003 | Giambattista et al. |
| 2003/0229317 A1 | 12/2003 | Ferguson et al. |
| 2004/0193110 A1 | 9/2004 | Giambattista et al. |
| 2004/0193120 A1 | 9/2004 | Ferguson et al. |
| 2004/0220524 A1 | 11/2004 | Sadowski et al. |
| 2005/0020979 A1 | 1/2005 | Westbye et al. |
| 2005/0080377 A1 | 4/2005 | Sadowski et al. |
| 2005/0101919 A1 | 5/2005 | Brunnberg |
| 2005/0171477 A1 | 8/2005 | Rubin et al. |
| 2005/0261634 A1 | 11/2005 | Karlsson |
| 2005/0277895 A1 | 12/2005 | Giambattista et al. |
| 2005/0283115 A1 | 12/2005 | Giambattista et al. |
| 2006/0100588 A1 | 5/2006 | Brunnberg et al. |
| 2006/0189933 A1 | 8/2006 | Alheidt et al. |
| 2006/0229569 A1 | 10/2006 | Lavi et al. |
| 2006/0229570 A1 | 10/2006 | Lovell et al. |
| 2006/0270984 A1 | 11/2006 | Hommann |
| 2006/0270986 A1 | 11/2006 | Hommann et al. |
| 2007/0100292 A1 | 5/2007 | Kirchhofer et al. |
| 2007/0135767 A1 | 6/2007 | Gillespie et al. |
| 2007/0149925 A1 | 6/2007 | Edwards et al. |
| 2007/0173772 A1 | 7/2007 | Liversidge |
| 2007/0293819 A1 | 12/2007 | Giambattista et al. |
| 2008/0021397 A1 | 1/2008 | Kirchhofer et al. |
| 2008/0021410 A1 | 1/2008 | Kirchhofer et al. |
| 2008/0058719 A1 | 3/2008 | Edwards et al. |
| 2008/0108951 A1 | 5/2008 | Jerde et al. |
| 2008/0114295 A1 | 5/2008 | Glynn |
| 2008/0140007 A1 | 6/2008 | Glynn |
| 2008/0147006 A1 | 6/2008 | Brunnberg et al. |
| 2008/0183140 A1 | 7/2008 | Paproski et al. |
| 2008/0188813 A1 | 8/2008 | Miller et al. |
| 2008/0228147 A1 | 9/2008 | David-Hegerich et al. |
| 2008/0262438 A1 | 10/2008 | Bollenbach et al. |
| 2008/0269692 A1 | 10/2008 | James et al. |
| 2009/0005735 A1 | 1/2009 | Wikner et al. |
| 2009/0005742 A1 | 1/2009 | Liversidge |
| 2009/0069753 A1 | 3/2009 | Ruan et al. |
| 2009/0082734 A1 | 3/2009 | Walters et al. |
| 2009/0171311 A1 | 7/2009 | Genosar et al. |
| 2009/0259194 A1 | 10/2009 | Pinedjian et al. |
| 2009/0270804 A1 | 10/2009 | Mesa et al. |
| 2009/0270814 A1 | 10/2009 | Masi et al. |
| 2010/0063457 A1 | 3/2010 | Crossman |
| 2010/0160894 A1 | 6/2010 | Julian et al. |
| 2010/0228193 A1 | 9/2010 | Wyrick |
| 2015/0051553 A1 * | 2/2015 | Bjork ................ A61M 5/3287 604/198 |

OTHER PUBLICATIONS

PCT International Search Report and Written Opinion in International Appln. No. PCT/EP2016/078252, dated Feb. 27, 2017, 9 pages.

* cited by examiner

CAP FOR AN INJECTION DEVICE

CROSS REFERENCE TO RELATED APPLICATIONS

The present application is the national stage entry of International Patent Application No. PCT/EP2016/078252, filed on Nov. 21, 2016, and claims priority to Application No. EP 15196681.9, filed in on Nov. 27, 2015, the disclosures of which are expressly incorporated herein in entirety by reference thereto.

TECHNICAL FIELD

The present disclosure relates to a cap for an injection device.

BACKGROUND

Injection devices, such as auto-injectors, are known in the art for dispensing a medicament to the injection site of a patient. Such injection devices typically comprise a body and a cap. A needle syringe is located in the body. The cap is removably attached to the body to shield the needle of the needle syringe. To dispense the medicament, the cap is first removed from the body to expose the needle. The needle is then inserted into the body of the patient at the injection site to dispense the medicament.

It is important that the cap is held onto the body with sufficient force to ensure that the cap is not accidentally removed from the body during transport and storage of the injection device. This ensures that the needle is kept sterile and also prevents the sharp needle from causing injury. However, the force required to hold the cap and body together can make it difficult for the patient to intentionally remove the cap from the body prior to injection, particularly if the patient is elderly or infirm.

SUMMARY

It is an object of the present disclosure to provide an improved injection device.

According to the present disclosure, there is provided a cap for an injection device having a body for holding a syringe with a needle extending from one end thereof, wherein the cap is removably attachable to the body and comprises: an actuator; a needle shield to cover said needle; and, a coupling between the actuator and the needle shield configured such that when the cap is attached to the body on an injection device, axial movement of the actuator away from the body causes rotation of the needle shield relative to the body.

Therefore, the actuator may be linearly pulled away from the body to remove the needle shield from the body. This pulling motion of the actuator may make removal of the needle shield easier for persons who may not have the dexterity required to twist the needle shield, such as the elderly and infirm.

In one embodiment, the coupling is configured such that when the cap is attached to the body of an injection device, axial movement of the actuator away from the body by a first distance causes axial movement of the needle shield away from the body by a second distance, which is smaller than the first distance. Therefore, if the actuator is pulled away from the body by a given force then the resultant force acting on the needle shield to urge the needle shield away from the body will be larger than said given force. Therefore, the coupling reduces the amount of force that must be exerted by the patient to remove the needle shield.

The coupling may comprise a connection between the actuator and the needle shield. The connection may be a threaded connection.

The cap may further comprise a holder, wherein the coupling comprises a first connection between the actuator and the needle shield and a second connection between the holder and the needle shield. In one embodiment, the first connection is configured such that when the cap is attached to the body of an injection device, axial movement of the actuator away from the body causes rotation of the needle shield relative to the body, and wherein the second connection is configured such that rotation of the needle shield relative to the body causes axial movement of the needle shield away from the body.

The first and second connections may comprise threaded connections. In one embodiment, the pitch of the first connection is different to the pitch of the second connection. Therefore, axial movement of the actuator away from the body by a first distance results in the needle shield moving away from to the body by a second distance. Preferably, the pitch of the first connection is greater than the pitch of the second connection. Therefore, the second distance is smaller than the first distance and thus, if a given force is exerted on the actuator to pull the actuator away from the body, then the resultant force acting on the needle shield to move the needle shield away from the body will be larger than said given force. Thus, the amount of force that must be exerted by the patient to remove the needle shield is reduced.

In one embodiment, the cap further comprises a lock that releasably couples the holder to the body to prevent rotation of the holder relative to the body. The lock may comprise one or more projections or recesses that are configured to engage with the body when the cap is attached to the body. In one embodiment, the injection device comprises a retractable sleeve and said one or more projections or recesses of the lock are configured to engage with the retractable sleeve.

In one embodiment, the actuator comprises a first stopper and the holder comprises a second stopper, wherein the first and second stoppers are configured such that when the cap is attached to the body the first and second stoppers engage when the actuator is moved away from the body to limit axial movement between the actuator and holder.

The actuator may comprise an end cap. In one such embodiment, the needle shield is disposed in the end cap when the cap is attached to the body. This allows for the injection device to be compact and easy to store.

The actuator may comprise a grip that may be gripped by the patient to move the actuator axially away from the body. The grip may comprise a flanged portion of the actuator.

According to the present disclosure, there is also provided an injection device comprising a body for holding a syringe having a needle extending from an end thereof and a cap.

In one embodiment, the injection device comprises a syringe held in the body and having a needle at one end, wherein the needle shield is configured to frictionally engage with the syringe when the cap is attached to the body, and wherein axial movement of the actuator away from the body causes rotation of the needle shield about the syringe. The rotational movement of the needle shield about the syringe may reduce static friction between the needle shield and the syringe to facilitate removal of the needle shield from the syringe. The syringe may contain a medicament.

In one embodiment, the needle shield comprises a spindle, wherein the coupling is between the actuator and the spindle.

In one embodiment, the injection device is an auto-injector.

According to the present disclosure, there is also provided a method of removing a cap from a body of an injection device, wherein the body holds a syringe having a needle extending from one end thereof and the cap comprises a needle shield to cover said needle, the method comprising: moving an actuator of the cap axially away from the body of the injection device, wherein the actuator is coupled to the needle shield by a coupling configured such that the axial movement of the actuator away from the body causes rotation of the needle shield relative to the body. The injection device may comprise one or more of the features of the injection device described hereinbefore.

These and other aspects of the invention will be apparent from and elucidated with reference to the embodiments described hereinafter.

BRIEF DESCRIPTION OF THE FIGURES

Embodiments of the invention will now be described, by way of example only, with reference to the accompanying drawings, in which.

DETAILED DESCRIPTION

Figure 1A:
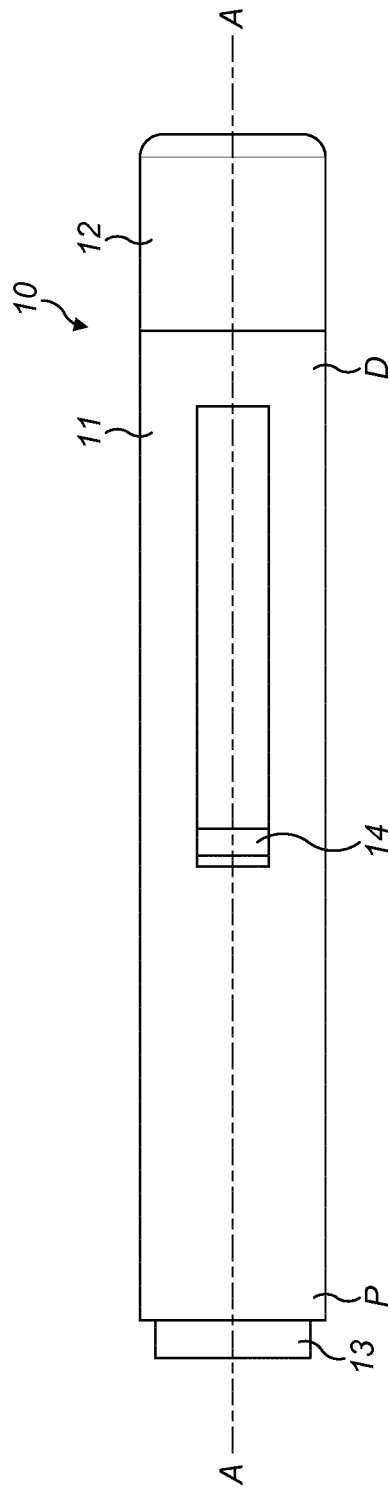
FIG. 1A is a schematic side view of an auto-injector that embodies the disclosure, with a cap attached to a body of the injection device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
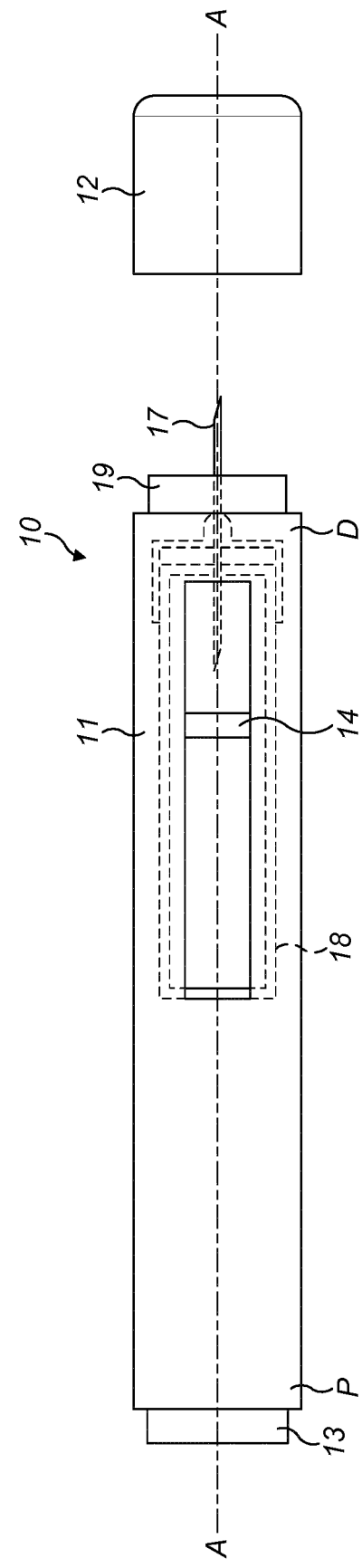
FIG. 1B is a schematic side view of the auto-injector of FIG. 1A, with the cap removed from the body.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2:
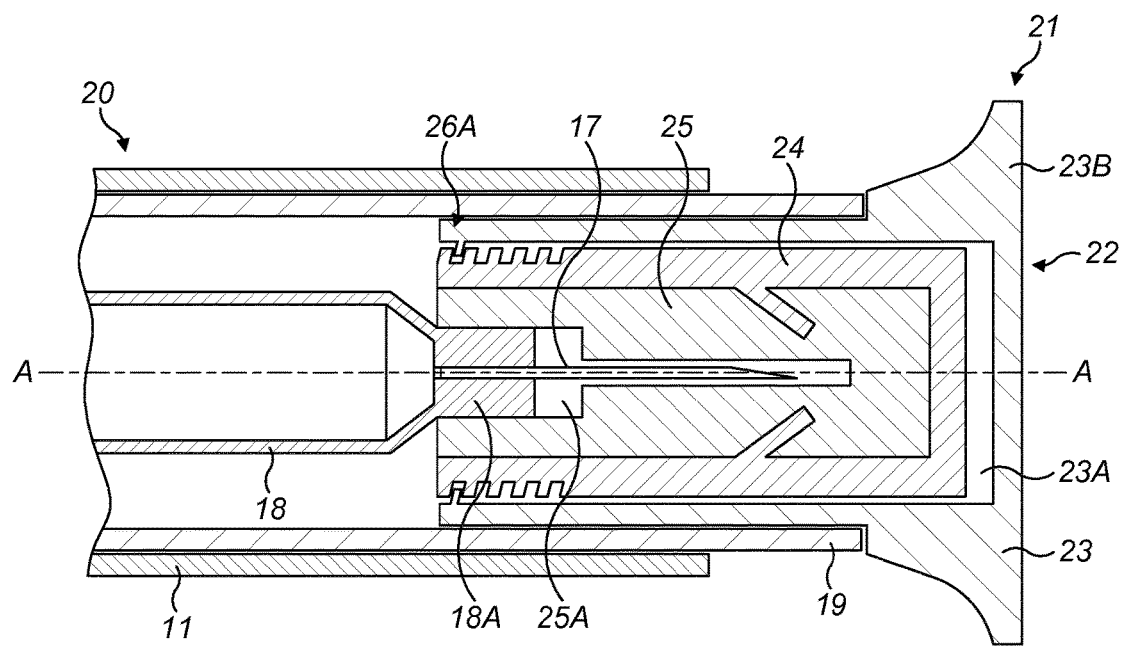
FIG. 2 is a schematic cross-sectional side view of part of a cap for an injection device according to a first embodiment of the disclosure, wherein a portion of the syringe is received in a needle shield.
Figure 3:
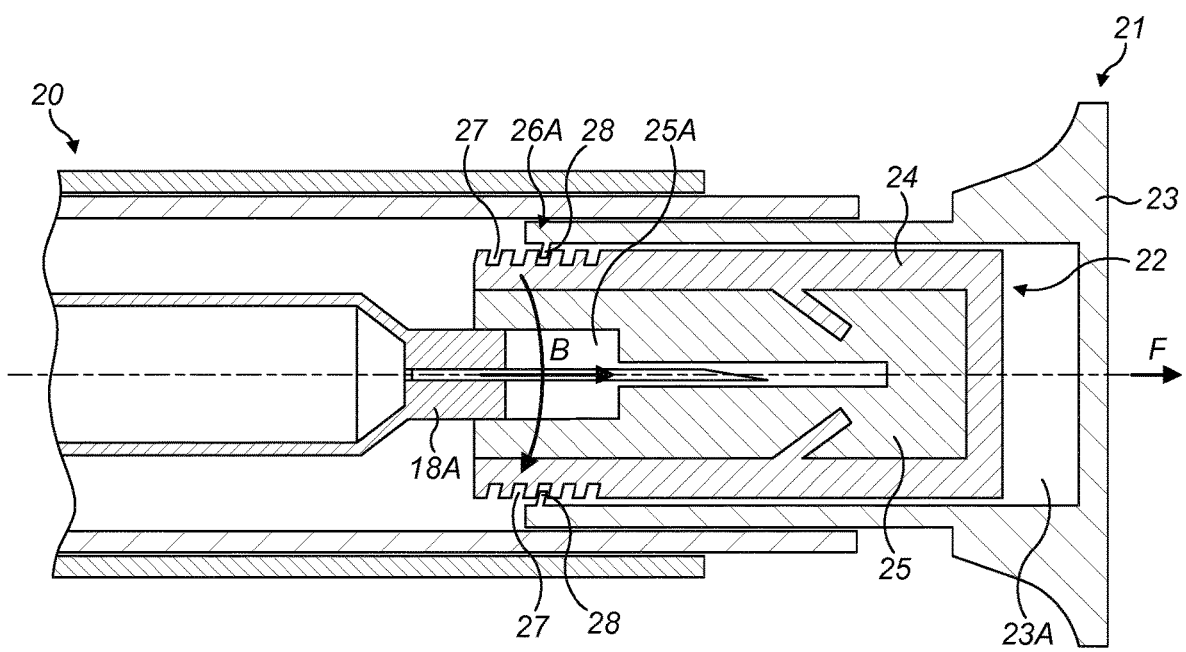
FIG. 3 is a schematic cross-sectional side view of the cap of FIG. 2, wherein said portion of the syringe is partially removed from the needle shield.
Figure 4:
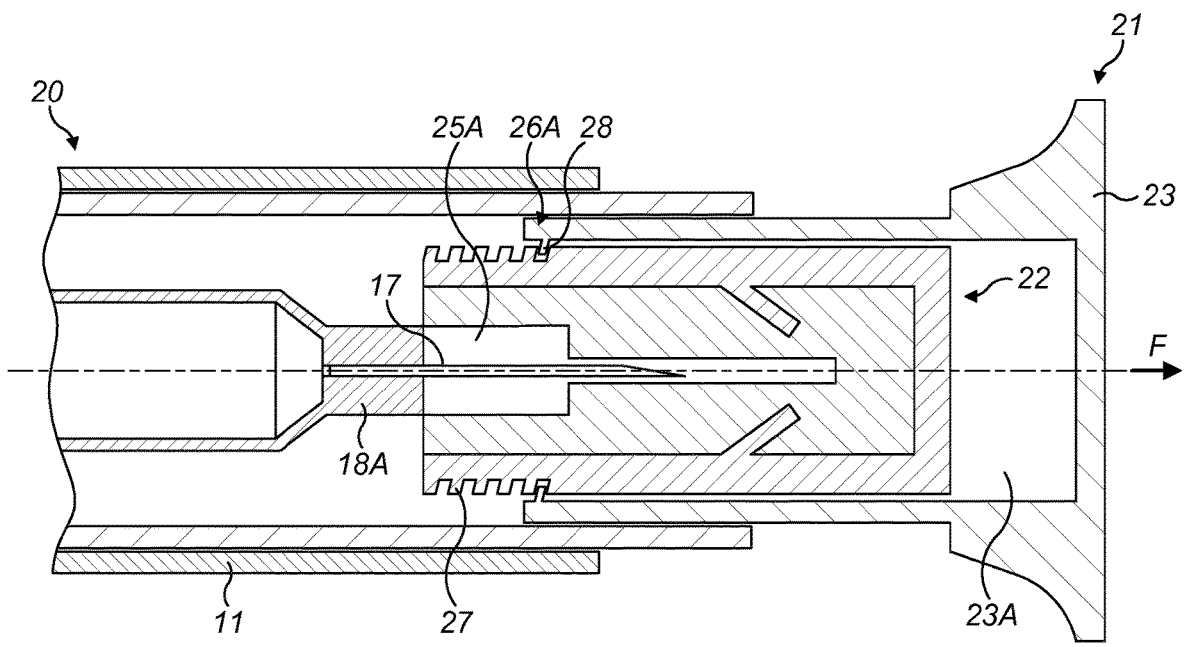
FIG. 4 is a schematic cross-sectional side view of the cap of FIG. 2, wherein said portion of the syringe is completely removed from the needle shield.

Referring now to FIGS. 2 to 4, part of an injection device 20 according to a first embodiment of the disclosure is shown. The injection device 20 is in the form of an auto-injector 20 that has similar features to the auto-injector 10 described above in relation to FIGS. 1A and 1B, with like features retaining the same reference numerals. A difference is that the cap 12 of the auto-injector 10 described above is omitted and is replaced with an alternative cap 21.

The cap 21 of the auto-injector 20 of the first embodiment of the disclosure comprises a needle shield 22 and an actuator 23. The needle shield 22 comprises a housing 24 and an inner sheath 25. The inner sheath 25 is fixedly secured in the housing 24. The inner sheath 25 comprises a cylindrical recess 25A. The recess 25A is configured to receive an end portion 18A of the syringe 18 such that the needle 17 is shielded by the inner sheath 25. The friction between the inner sheath 25 and the end portion 18A of the syringe 18 is sufficient to hold the needle shield 22 in place covering the needle 17.

The actuator 23 is in the form of an end cap 23. The end cap 23 comprises a cylindrical recess 23A at one end and a grip at the other end in the form of a flanged portion 23B. The flanged portion 23B facilitates gripping of the end cap 23 to remove the cap 21 from the body 11 of the auto-injector 20. The housing 24 of the needle shield 22 is generally cylindrical and is received within the recess 23A of the end cap 23.

The auto-injector 20 further comprises a coupling between the needle shield 22 and the end cap 23. The coupling comprises a connection 26A having a screw thread 27 and a pair of projections 28.

The screw thread 27 is formed into a peripheral surface of the housing 24 of the needle shield 22 and extends about the central axis A-A of the auto-injector 20. The projections 28 protrude from opposing sides of the inner surface of the end cap 23 to extend radially into the recess 23A of the end cap 23. Thus, the projections 28 engage with the screw thread 27 when the needle shield 22 is received in the recess 23A of the end cap 23.

The connection 26A is configured such that axial movement of the end cap 23 away from the body 11 causes the projections 28 to engage with the screw thread 27 such that the needle shield 22 rotates relative to the body 11 about the central axis A-A (in the direction of arrow 'B' shown in FIG. 3). Axial movement of the end cap 23 away from the body 11 also causes the needle shield 22 to move axially away from the body 11 (in the direction of arrow 'F' in FIG. 3).

The cap 21 is initially attached to the body 11 such that the end portion 18A of the syringe 18 is completely received in the recess 25A of the inner sheath 25 (as shown in FIG. 2). Thus, the needle 17 is covered by the needle shield 22 to keep the needle 17 sterile and to prevent the needle 17 from causing injury to the patient.

To inject a medicament, the cap 21 must first be removed from the body 11 to expose the needle 17. Removal of the cap 21 from the body 11 is achieved by the patient holding the body 11 in one hand and exerting a force on the end cap 23 with the other hand (in the direction of arrow 'F' shown in FIGS. 3 and 4) to pull the end cap 23 away from the body 11. This causes the projections 28 to be urged relative to the needle shield 22 (in the direction of arrow 'F') such that the projections 28 exert a force on the screw thread 27 which results in the needle shield 22 rotating about the central axis A-A relative to the body 11 and end cap 23. The needle shield 22 also moves axially away from the body 11 as the end cap 23 is pulled away from the body 11.

The needle 17 is fixed relative to the body 11. Therefore, as the end cap 23 is pulled away from the body 11, the needle shield 22 moves axially away from the needle 17 such that it first becomes partially removed from the end portion 18A of the syringe 18 (as shown in FIG. 3) and then becomes fully removed from the end portion 18A of the syringe 18 such that the end portion 18A is no longer received in the recess 25A of the inner sheath 25 (as shown in FIG. 4). Once the end portion 18A of the syringe 18 has been fully removed from the recess 25A in the inner sheath 25, the friction between the cap 21 and the body 11 is reduced such that the cap 21 can easily be removed from the body 11.

The rotational movement of the needle shield 22 relative to the end portion 18A of the syringe 18 when the end cap 23 is moved axially away from the body 11 overcomes the static friction between the inner sheath 25 and the end portion 18A, making it easier to remove the cap 21 from the body 11. The linear pulling motion (in the direction of arrow 'F') of the end cap 23 relative to the body 11 makes removal of the cap 21 easier for the elderly and infirm, who may not have the dexterity required to manually twist the cap 21 relative to the body 11.

Although in the above described embodiment the housing 24 of the needle shield 22 comprises the screw thread 27 and the end cap 23 comprises the pair of projections 28, in an alternative embodiment (not shown) the needle shield comprises the pair of projections and the end cap comprises the screw thread. In another alternative embodiment, the first pair of projections are omitted and are replaced by a second screw thread that is configured to engage with the first screw thread.

In the above described embodiment the end cap 23 comprises a flanged portion 23B which facilitates gripping of the end cap 23 to remove the cap 21 from the body 11 of the auto-injector 20. However, in alternative embodiments (not shown) the flanged portion 23B is omitted. In one such alternative embodiment, the end cap comprises a loop of material that may be gripped by the user to pull the end cap away from the body. The end cap may comprise a cylindrical portion for receiving the needle shield and the loop of material may be secured to the cylindrical portion. In another embodiment (not shown), the end cap comprises a hook or handle that may be gripped by the user to pull the end cap away from the body.

Figure 5:
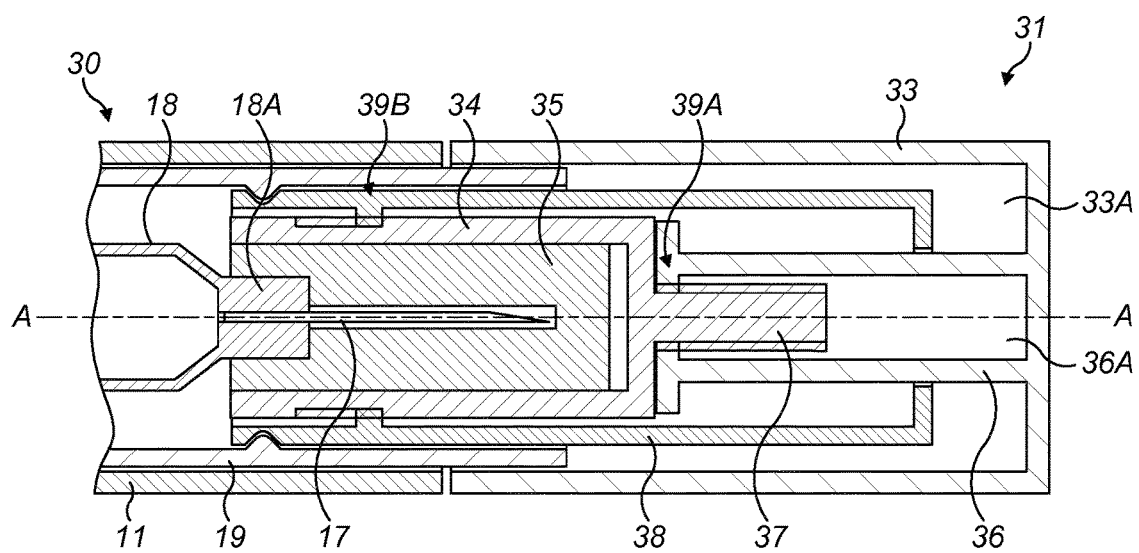
FIG. 5 is a schematic cross-sectional side view of part of a cap for an injection device according to a second embodiment of the disclosure, wherein an actuator is positioned proximate to a body of the injection device.
Figure 6:
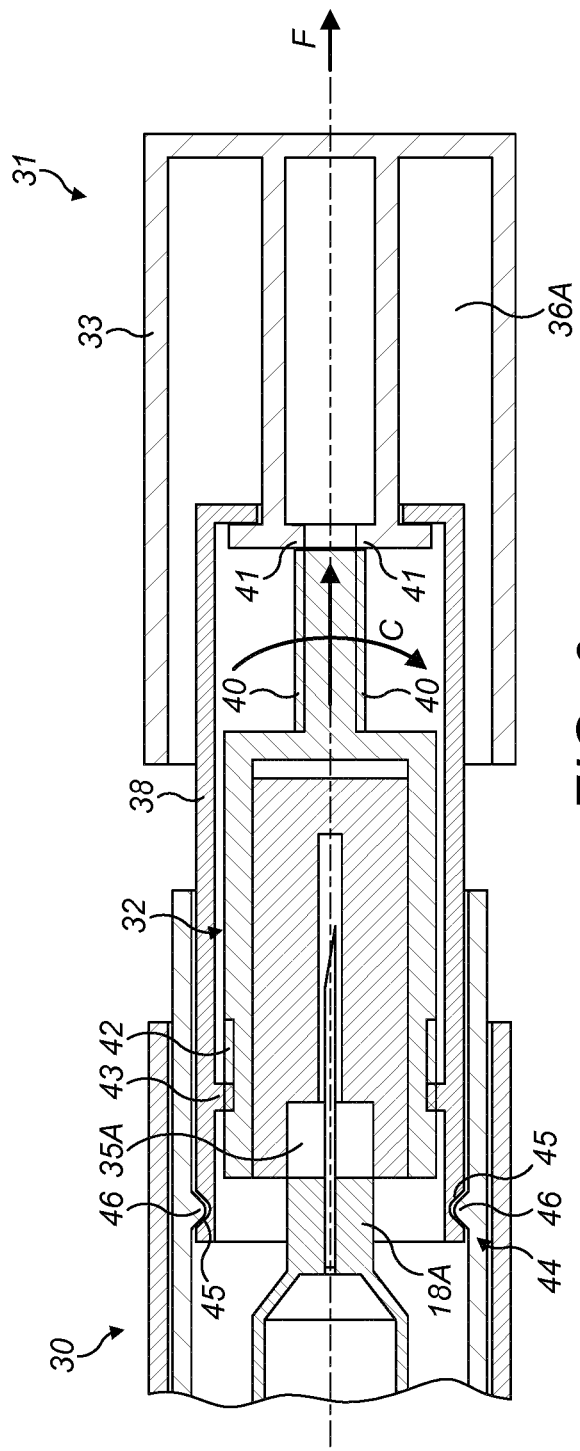
FIG. 6 is a schematic cross-sectional side view of the cap of FIG. 5, wherein the actuator is moved away from the body; and, FIG. 7 is a schematic cross-sectional side view of the cap of FIG. 5, wherein the actuator is moved further away from the body.
Figure 7:
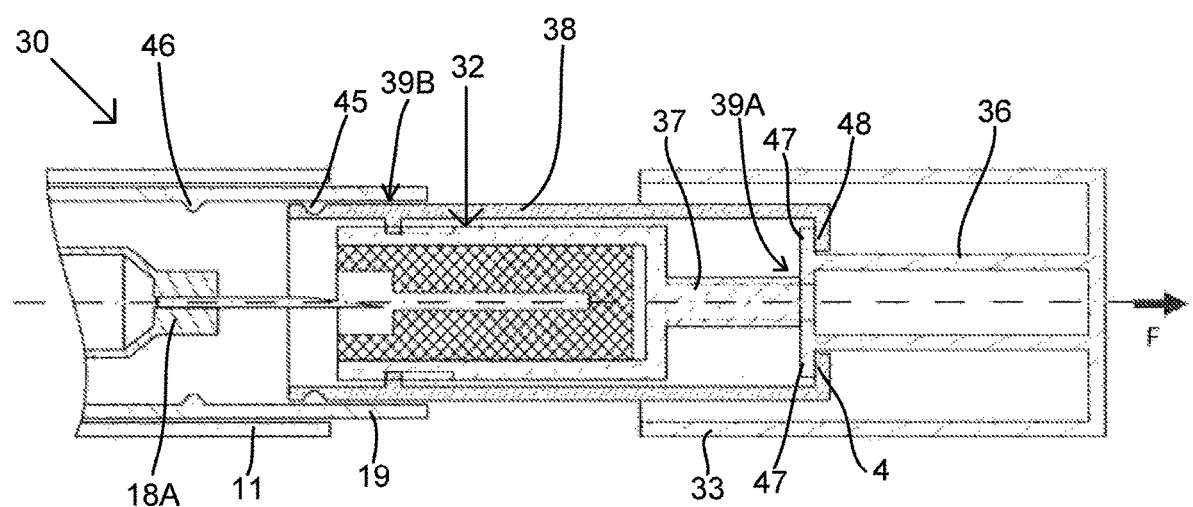

Referring now to FIGS. 5 to 7, an injection device 30 according to a second embodiment of the disclosure is shown. The injection device 30 is in the form of an auto-injector 30 that has similar features to the auto-injector 10 described above in relation to FIGS. 1A and 1B, with like features retaining the same reference numerals. A difference is that the cap 12 of the auto-injector 10 described above is omitted and is replaced with an alternative cap 31.

The cap 31 of the auto-injector 30 of the second embodiment of the disclosure comprises a needle shield 32 and an actuator 33. The needle shield 32 comprises a housing 34 and an inner sheath 35. The housing 34 is generally cylindrical. The inner sheath 35 is fixedly secured in the housing 34. The inner sheath 35 comprises a cylindrical recess 35A. The recess 35A is configured to receive end portion 18A of the syringe 18 such that the needle 17 is shielded by the inner sheath 35. The friction between the inner sheath 35 and the end portion 18A of the syringe 18 is sufficient to hold the needle shield 32 in place covering the needle 17.

The actuator 33 is in the form of an end cap 33. The end cap 33 comprises a cylindrical recess 33A.

The cap 31 further comprises a support member 36, a spindle 37 and a holder 38. The support member 36 is tubular and extends into the recess 33A of the end cap 33 from the end of the end cap 33. The support member 36 defines a recess 36A that is configured to receive the spindle 37. The support member 36 is co-axial with the end cap 33 and is integrally formed therewith.

The spindle 37 is generally cylindrical and extends from an end of the housing 34 of the needle shield 32. The spindle 37 is part of the needle shield 32 and is co-axial and integrally formed with the housing 34.

The holder 38 is a hollow tube. An end of the holder 38 is configured to receive the support member 36 such that part of the holder 38 towards said end is located between the support member 36 and a peripheral wall of the end cap 33. The needle shield 32 is received within the holder 38 such that the spindle 37 is located in the recess 36A of the support member 36 when the inner sheath 35 is received on the end portion 18A of the syringe 18 (as shown in FIG. 5).

The auto-injector 30 further comprises a coupling between the needle shield 32 and the end cap 33. The coupling comprises first and second connections 39A, 39B.

The first connection 39A comprises a first screw thread 40 and a first pair of projections 41. The first screw thread 40 is formed into a peripheral surface of the spindle 37 and extends about the central axis A-A of the auto-injector 30. The first pair of projections 41 protrude from opposing sides of an end of the support member 36 to extend radially towards the central axis A-A of the auto-injector 30. Thus, the first pair of projections 41 engage with the first screw thread 40 when the spindle 37 is received in the recess 36A in the support member 36.

The first connection 39A is configured such that axial movement of the end cap 33 away from the body 11 causes the first pair of projections 41 to engage with the first screw thread 40 such that the spindle 37 rotates relative to the body 11, end cap 33, and holder 38 about the central axis A-A (in the direction of arrow 'C' shown in FIG. 6). Axial movement of the end cap 33 away from the body 11 also causes the end cap 33 to move axially away from the spindle 37 (in the direction of arrow 'F' in FIG. 6) as the spindle 37 rotates relative to the end cap 33.

The second connection 39B comprises a second screw thread 42 and a second pair of projections 43. The second screw thread 42 is formed into a peripheral surface of the housing 34 of the needle shield 32 and extends about the central axis A-A of the auto-injector 30. The second pair of projections 43 protrude from opposing sides of an inner surface of the holder 38 to extend towards the central axis A-A of the auto-injector 30. Thus, the second pair of projections 43 engage with the second screw thread 42 when the needle shield 32 is received in the holder 38.

The second connection 39B is configured such that rotation of the needle shield 32 relative to the holder 38 causes the second pair of projections 43 to engage with the second screw thread 42 such that the needle shield 32 moves axially relative to the body 11 and holder 38 in a direction away from the body 11 (in the direction of arrow 'F' shown in FIG. 6).

The cap 31 is initially attached to the body 11 such that the end portion 18A of the syringe 18 is completely received in the recess 35A of the inner sheath 35 (as shown in FIG. 5). Thus, the needle 17 is covered by the needle shield 32 to keep the needle 17 sterile and to prevent the needle 17 from causing injury to the patient.

To inject medicament, the cap 31 must first be removed from the body 11 to expose the needle 17. Removal of the cap 31 from the body 11 is achieved by the patient holding the body 11 in one hand and exerting a force on the end cap 33 with the other hand (in the direction of arrow 'F' shown in FIGS. 6 and 7) to pull the end cap 33 away from the body 11. This causes the first pair of projections 41 to be urged relative to the spindle 37 (in the direction of arrow 'F') such that the first pair of projections 41 exert a force on the first screw thread 40 which results in the spindle 37 rotating about the central axis A-A relative to the body 11, holder 38, and end cap 33. The end cap 33 also moves axially away from the spindle 37 as the first pair of projections 41 move relative to the first screw thread 40.

The spindle 37 is integrally formed with the housing 34 of the needle shield 32 such that rotation of the spindle 37 causes rotation of the housing 34 and needle sheath 35. Thus, when the spindle 37 rotates due to the patient pulling on the end cap 33, the second screw thread 42 engages with the second pair of projections 43 to urge the needle shield 32 axially relative to the holder 38 (in the direction of arrow 'F' in FIGS. 6 and 7). The holder 38 is fixed axially and rotationally relative to the body 11 by a lock 44. The lock 44 comprises a plurality of recesses 45 in the holder 38 and a plurality of protuberances 46 on the retractable sleeve 19 that engage with the plurality of recesses 45. Therefore, when the needle shield 32 rotates and moves axially relative to the holder 38, the needle shield 32 rotates and moves axially away from the body 11 (in the direction of arrow 'F' in FIGS. 6 and 7).

The needle 17 is fixed relative to the body 11. Therefore, when the end cap 33 is pulled away from the body 11 by the patient, the needle shield 32 rotates and moves axially away from the needle 17 such that it first becomes partially removed from the end portion 18A of the syringe 18 (as shown in FIG. 6) and then becomes fully removed from the end portion 18A such that the end portion 18A is no longer received in the recess 35A of the inner sheath 35 (as shown in FIG. 7).

Once the end portion 18A of the syringe 18 has been fully removed from the recess 35A in the inner sheath 35, the friction between the cap 31 and the body 11 is reduced such that the cap 31 can easily be removed from the body 11. This is achieved by pulling the end cap 33 away from the body 11 such that the holder 38 is urged away from the body 11, which results in the protuberances 46 disengaging with the recesses 45 such that the holder 38 is separated from the retractable sleeve 19. The support member 36 has a first stopper 47 that engages with a second stopper 48 of the holder 38. The first stopper 47 is in the form of an annular lip that extends radially outwardly and the second stopper 48 is in the form on an annular lip that extends radially inwardly. The first and second stoppers 47, 48 are configured to limit the range of axial movement between the end cap 33 and holder 38 such that pulling on the end cap 33 exerts an axial force on the holder 38 that urges the holder 38 away from the body 11.

The rotational movement of the needle shield 32 relative to the end portion 18A of the syringe 18 when the end cap 33 is moved axially away from the body 11 overcomes the static friction between the inner sheath 35 and the end portion 18A, making it easier to remove the cap 31 from the body 11. The linear pulling motion (in the direction of arrow 'F') of the end cap 33 relative to the body 11 makes removal of the cap 31 easier for the elderly and infirm, who may not have the dexterity required to manually twist the cap 31 relative to the body 11.

The first screw thread 40 has a higher pitch than the second screw thread 42 such that axial movement of the end cap 33 relative to the needle shield 32 by a first distance, due to the end cap 33 being pulled away from the body 11 (in the direction of arrow 'F'), results in the needle shield 32 moving axially relative to the body 11 and holder 38 by a second distance that is smaller than the first distance. This configuration of the first and second screw threads 40, 42 means that if the end cap 33 is pulled away from the body 11 by a given force then the resultant force acting on the needle shield 32 to urge the needle shield 32 away from the end portion 18A of the syringe 18 will be larger than said given force. Therefore, the coupling reduces the amount of force that must be exerted by the patient to remove the cap 31 from the body 11.

Although in the second embodiment the first connection 39A comprises the first screw thread 40 on the spindle 37 and a first pair of projections 41 on the support member 36, in an alternative embodiment (not shown) the first pair of projections are provided on the spindle and the support member comprises the first screw thread. Similarly, in another alternative embodiment (not shown) the second pair of projections are provided on the housing of the needle shield and the holder comprises the second screw thread. In yet another embodiment, the first and/or second pairs of projections are omitted and are replaced by corresponding third and/or fourth screw threads that are configured to engage with the first/and or second screw threads respectively. In another alternative embodiment (not shown) the first and second screw threads are omitted and are each replaced by a corresponding pair of tracks that receive the projections. The pairs of tracks are angled with respect to the central axis of the auto injector such that movement of the projections in the direction of the central axis relative to the tracks results in rotation of the tracks relative to the projections about the central axis.

Although in the above described embodiments the actuator 23, 33 comprises an end cap 23, 33, in alternative embodiments (not shown) the actuator comprises a different type of component, for example, an outer ring that circumscribes the needle shield and is slid in the axial direction to relative to the needle shield to urge the needle shield to rotate relative to the body.

Although in the above described embodiments the injection device 20, 30 is in the form of an auto-injector 20, 30, in alternative embodiments (not shown) the injection device 20, 30 comprises a different type of drug delivery device.

Although in the above described embodiments the needle shield 22, 32 comprises a housing 24, 34 and a separate inner sheath 25, 35 that is received in the housing 24, 34, in an alternative embodiments (not shown) the housing is omitted or is integrally formed with the inner sheath.

It should be noted that in FIGS. 2 to 7 the screw threads 27, 40, 42 are shown schematically and therefore appear to have a relatively low pitch. However, it should be recognised that in certain arrangements the screw threads may require a higher pitch than is shown to ensure that axial movement of the actuator away from the body results in rotation of the needle shield relative to the body.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days).

In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. A cap for an injection device having a body for holding a syringe with a needle extending from one end thereof, wherein the cap is removably attachable to the body and comprises:
   an actuator;
   a needle shield to cover the needle; and
   a coupling between the actuator and the needle shield configured such that when the cap is attached to the body of the injection device, an axial movement of the actuator away from the body along a longitudinal axis of the body causes rotation of the needle shield relative to the body and an axial displacement of the needle shield relative to the needle.

2. The cap according to claim 1, wherein the coupling is configured such that when the cap is attached to the body of the injection device, the axial movement of the actuator away from the body by a first distance causes the axial movement of the needle shield away from the body by a second distance, which is smaller than the first distance.

3. The cap according to claim 1, wherein the coupling comprises a connection between the actuator and the needle shield.

4. The cap according to claim 3, wherein the connection is a threaded connection.

5. The cap according to claim 1, further comprising a holder, wherein the coupling comprises a first connection between the actuator and the needle shield and a second connection between the holder and the needle shield.

6. The cap according to claim 5, wherein the first connection is configured such that when the cap is attached to the body of the injection device, the axial movement of the actuator away from the body causes rotation of the needle shield relative to the body, and wherein the second connection is configured such that rotation of the needle shield relative to the body causes the axial movement of the needle shield away from the body.

7. The cap according to claim 5, wherein the first and second connections comprise threaded connections.

8. The cap according to claim 7, wherein a pitch of the first connection is different from a pitch of the second connection.

9. The cap according to claim 8, wherein the pitch of the first connection is greater than the pitch of the second connection.

10. The cap according to claim 5, further comprising a lock that releasably couples the holder to the body to prevent rotation of the holder relative to the body.

11. The cap according to claim 5, wherein the actuator comprises a first stopper and the holder comprises a second stopper, wherein the first and second stoppers are configured such that when the cap is attached to the body, the first and second stoppers engage when the actuator is moved away from the body to limit axial movement between the actuator and holder.

12. The cap according to claim 1, wherein the actuator comprises an end cap.

13. The cap according to claim 12, wherein the needle shield is disposed in the end cap when the cap is attached to the body.

14. An injection device comprising:
   a body for holding a syringe with a needle extending from one end thereof; and
   a cap that is removably attachable to the body, the cap comprising:
      an actuator;
      a needle shield to cover the needle; and
      a coupling between the actuator and the needle shield configured such that when the cap is attached to the body of the injection device, an axial movement of the actuator away from the body along a longitudinal axis of the body causes rotation of the needle shield relative to the body,
   wherein the needle shield is configured to frictionally engage with the syringe when the cap is attached to the body, and wherein the axial movement of the actuator away from the body causes rotation of the needle shield about the syringe.

15. The injection device according to claim 14, wherein the syringe contains a medicament.

16. The injection device according to claim 14, wherein the injection device is an auto-injector.

17. A method of removing a cap from a body of an injection device, wherein the body holds a syringe having a needle extending from one end thereof, and the cap comprises a needle shield to cover the needle, the method comprising:
   moving an actuator of the cap axially away from the body of the injection device along a longitudinal axis of the body, wherein the actuator is coupled to the needle shield by a coupling configured such that the axial movement of the actuator away from the body causes rotation of the needle shield relative to the body and relative to the needle.

* * * * *

UNITED STATES PATENT AND TRADEMARK OFFICE
CERTIFICATE OF CORRECTION

| | |
|---|---|
| PATENT NO. | : 11,058,825 B2 |
| APPLICATION NO. | : 15/778277 |
| DATED | : July 13, 2021 |
| INVENTOR(S) | : Wendland et al. |

It is certified that error appears in the above-identified patent and that said Letters Patent is hereby corrected as shown below:

In the Specification

In Column 1, Line 9, delete "in on" and insert -- on --

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*